United States Patent [19]

Wierzbicki et al.

[11] Patent Number: 5,266,591
[45] Date of Patent: Nov. 30, 1993

[54] ETHANOLAMINE BENZOATE COMPOUNDS

[75] Inventors: Michel Wierzbicki, L'Etang La Ville; Pierre Hugon, Rueil Malmaison; Jacques Duhault, Croissy Sur Seine; Michelle Boulanger, Marly Le Roi; Françoise Lacour, Vincennes, all of France

[73] Assignee: Adir et Compagnie, Courbevoie, France

[21] Appl. No.: 979,202

[22] Filed: Nov. 20, 1992

[30] Foreign Application Priority Data

Nov. 22, 1991 [FR] France ............................ 91 14357

[51] Int. Cl.$^5$ .............................................. A61K 31/24
[52] U.S. Cl. .................................... 514/539; 514/540; 560/36; 560/37; 560/41
[58] Field of Search ............................ 560/36, 37, 41; 514/539, 540

[56] References Cited

U.S. PATENT DOCUMENTS 4,237,165 12/1980 Duhalt .............................. 514/534

Primary Examiner—Paul J. Killos
Assistant Examiner—Samuel Barts
Attorney, Agent, or Firm—Gordon W. Hueschen

[57] ABSTRACT

The compounds are ethanolamine benzoate compounds useful for the treatment of syndrome X, and of hypertension in patients who are insulin resistant or have one or more metabolic anomalies.

A compound disclosed is S-1-(m-trifluoromethylphenyl) - 2 - {β - {4 - [2 - (N - (3,3 - diphenylpropionyl)-amino)éthyl]benzoyloxy}ethylamino} propane.

5 Claims, No Drawings

ETHANOLAMINE BENZOATE COMPOUNDS

The present invention relates to new ethanolamine benzoate compounds, a process for their preparation and pharmaceutical compositions containing them.

It relates especially to ethanolamine benzoate compounds of formula I:

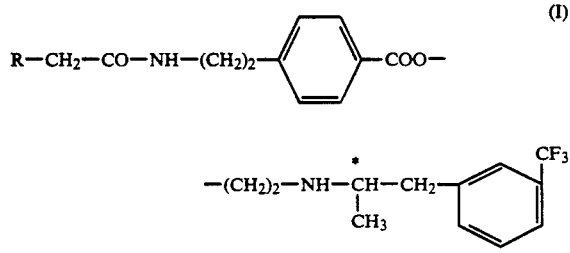

wherein R represents:
a) either a radical of the formula:

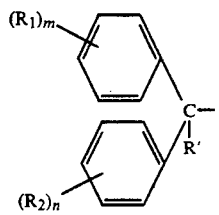

wherein:
R' represents a hydrogen atom or a straight-chain or branched alkyl radical containing from 1 to 5 carbon atoms,
$R_1$ and $R_2$, which are the same or different, each represents a hydrogen atom or a straight-chain or branched alkyl or alkoxy radical each having from 1 to 5 carbon atoms, and
m and n, which are the same or different, each represents 1, 2 or 3;
b) or a fluorenyl radical of the formula:

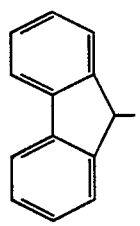

in the form of a racemic compound or of enantiomers.

The prior art is illustrated especially:
by French Patents Nos. 1 517 587 and 6564 M which relate, respectively, to:
compounds of formula A:

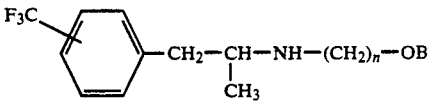

wherein:
represents, inter alia, the value 2, and
B represents a hydrogen atom or a group COB', B' being, inter alia, an optionally substituted phenyl radical, and
the use of compounds A as medicaments in the treatment of obesity, pain and epilepsy; and
by U.S. Pat. No. 4 237 165, which relates to pharmaceutical compositions containing either 1-(3-trifluoromethylphenyl)-2-($\beta$-hydroxyethylamino)propane or 1-(3-trifluoromethylphenyl)-2-($\beta$-benzoyloxyethylamino)propane, which can be used in the treatment of metabolism disorders.

Substantial structural modifications have resulted in the compounds of formula I of the present invention, which regulate the metabolism of glucides and lipids and counter the oxidation of LDLs (low-density lipoproteins), which is not true of the prior art compounds mentioned above which are themselves inactive with respect to LDL oxidation.

The present invention relates also to a process for the preparation of compounds of formula I which is characterised in that:
the acid of formula II:

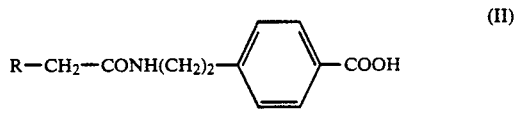

wherein R is as defined hereinbefore, is converted into a salt of formula II':

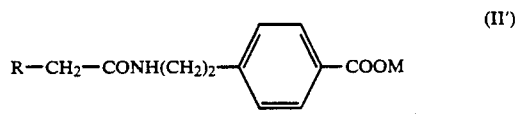

wherein R is as defined hereinbefore and M represents an alkali metal or alkaline earth metal;
the latter is reacted with a halogenated compound of formula III:

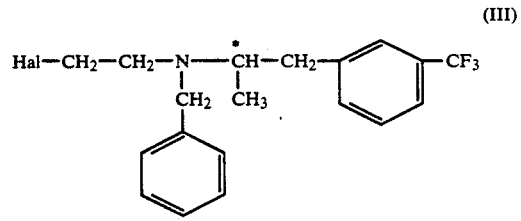

wherein Hal represents a halogen atom such as chlorine, bromine or iodine;
and the compound so-obtained of formula IV:

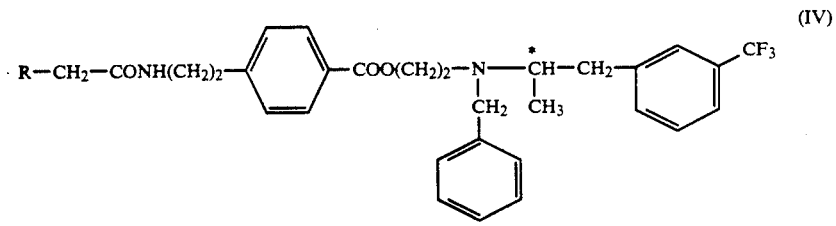

wherein R is as defined hereinbefore, is catalytically debenzylated.

Some starting materials of the general formula II are known. This is true of the acids of formula II wherein R represents:
either a benzhydryl radical, cf.: European Journal of Pharmacology (1987), 141-2, 243-251;
or a fluoren-9-yl radical, cf. U.S. Pat. No. 4,136,197.

The starting materials of formula II wherein R represents a substituted benzhydryl group of the formula:

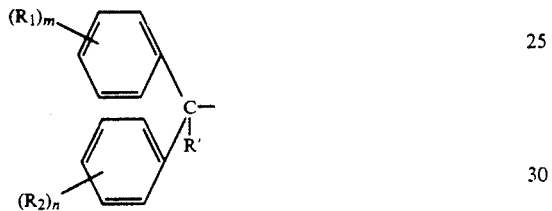

wherein:
m and n are as defined hereinbefore and
$R_1$, $R_2$ and $R'$ are as defined hereinbefore but, in addition, never simultaneously represent hydrogen, that is to say starting materials corresponding more precisely to formula IIa:

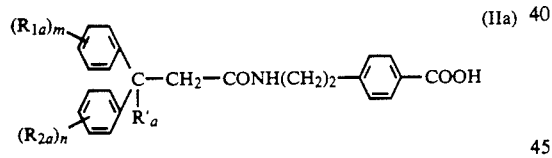

wherein:
m and n are as defined hereinbefore,
$R'_a$ represents a hydrogen atom or a straight-chain or branched alkyl radical containing from 1 to 5 carbon atoms,
$R_{1a}$ and $R_{2a}$, which are the same or different, each represents a hydrogen atom or a straight-chain or branched alkyl or alkoxy radical each having from 1 to 5 carbon atoms, but with the proviso that $R_{1a}$, $R_{2a}$ and $R'_a$ never simultaneously represent a hydrogen atom, were prepared by converting acids of formula V:

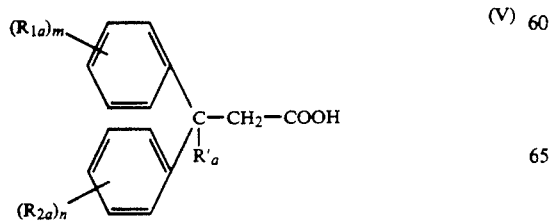

wherein: $R'_a$, $R_{1a}$ and $R_{2a}$, m and n are as defined hereinbefore, into the acid chloride or mixed anhydride of formula Va or Vb respectively:

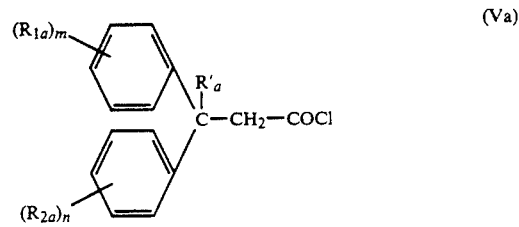

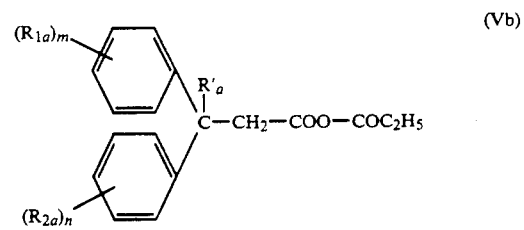

which are condensed
a) either with an amino acid of formula VIa:

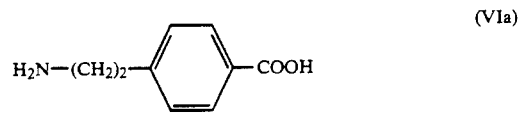

to yield a compound of formula IIa directly, which formula can be drawn more accurately as follows:

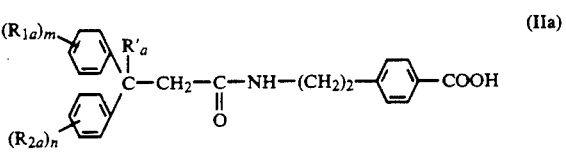

wherein $R'_a$, $R_{1a}$ and $R_{2a}$, m and n are as defined hereinbefore,
b) or with an amino ester of formula VIb:

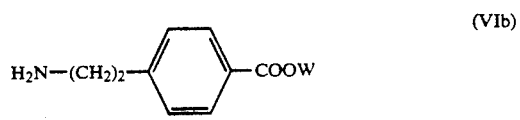

wherein W represents a straight-chain or branched alkyl radical having from 1 to 5 carbon atoms, to yield a compound of formula II'a:

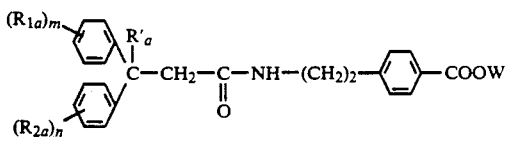

wherein R'$_a$, R$_{1a}$ and R$_{2a}$, m, n and w are as defined hereinbefore, which is hydrolysed to yield an acid of formula IIa.

When R'$_a$ represents a hydrogen atom, the corresponding acids V have themselves been obtained by HORNER reaction between the ketone of formula B:

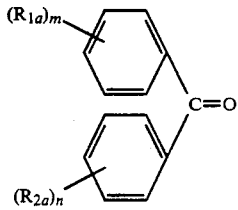

and ethyl phosphonoacetate [(CH$_2$H$_5$O)$_2$OP—CH$_2$—COOC$_2$H$_5$], followed by catalytic hydrogenation of the so-formed compound of formula C:

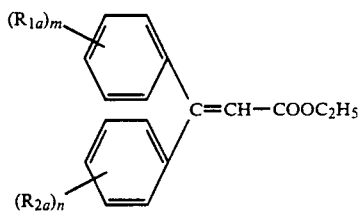

to yield the ester of formula D:

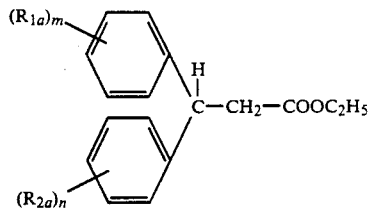

which is then hydrolysed to form the corresponding acid of formula E:

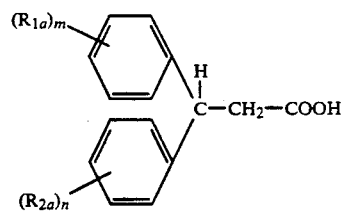

(R$_{1a}$, R$_{2a}$, m and n in all the formulae being as defined hereinbefore), that is to say the acid V in which R'$_a$ represents a hydrogen atom.

When R'$_a$ represents a straight-chain or branched alkyl radical containing from 1 to 5 carbon atoms, the corresponding acids V have themselves been obtained by COPE condensation between the ketone of formula F:

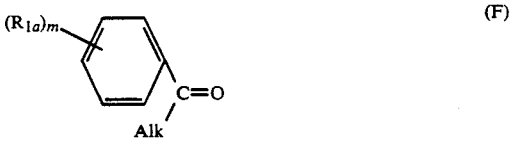

(wherein R$_{1a}$ and m are as defined hereinbefore and Alk represents a straight-chain or branched alkyl radical containing from 1 to 5 carbon atoms) and ethyl cyanoacetate (NC—CH$_2$—COOC$_2$H$_5$) in toluene, in the presence of acetic acid and ammonium acetate, to yield the ethylenic compound of formula G:

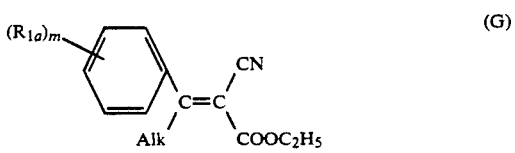

when is then subjected to the action of an organomagnesium compound of formula H:

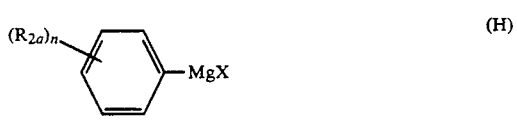

(R$_{2a}$ and n being as defined hereinbefore and X representing a halogen atom), to yield the compound of formula J:

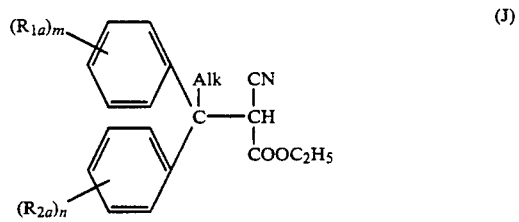

(wherein R$_{1a}$, R$_{2a}$, m, n and Alk are as defined hereinbefore), which compound J is hydrolysed to form the acid of formula K:

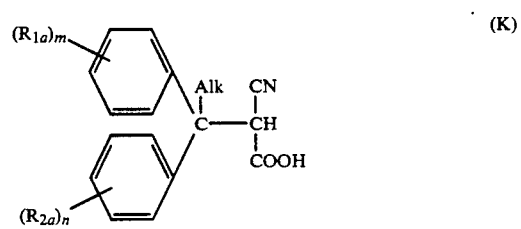

which is decarboxylated to yield the nitrile of formula L:

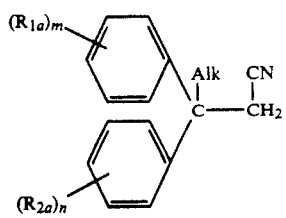
(L)

which is in turn hydrolysed to yield the desired acid of formula M:

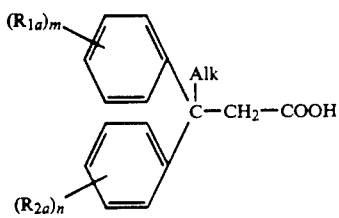
(M)

(wherein $R_{1a}$, $R_{2a}$, m, n and Alk are as defined hereinbefore); that is to say to form the acid of formula V in which $R'_a$ represents a straight-chain or branched alkyl radical containing from 1 to 5 carbon atoms.

The starting materials of formula III:

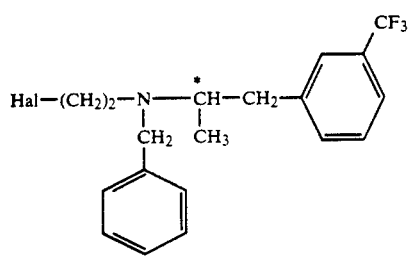
(III)

wherein Hal is as defined hereinbefore were prepared: by reacting (RS)-, (R)- or (S)-1-m-trifluoromethylphenyl-2-benzylaminopropane of formula N:

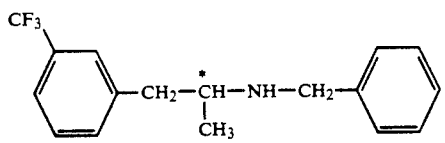
(N)

with a halogenated compound of formula P:

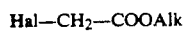
(P)

wherein Hal is as defined hereinbefore and Alk represents an alkyl radical having from 1 to 3 carbon atoms, to yield the glycinate of formula Q:

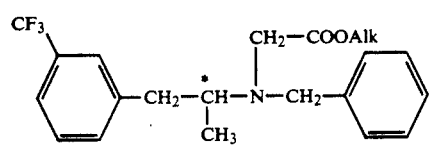
(Q)

which can be converted into the corresponding glycine of formula T:

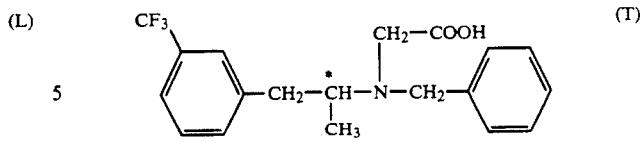
(T)

which compounds of formula Q and T, subjected to reduction by means of $LiAlH_4$ in ether, yield the (RS), (R) or (S) compound of formula U:

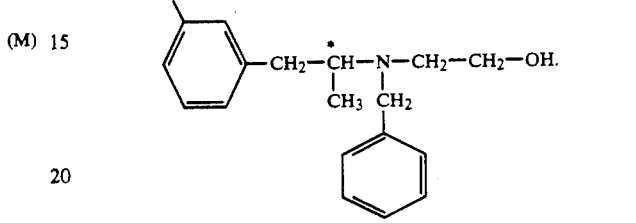
(U)

The latter is then converted into the halide III by means of a halogenated compound, such as, for example, $SOCl_2$, $PCl_5$ or $POCl_3$.

The (S)- and (R)-1-m-trifluoromethylphenyl-2-benzylaminopropanes of formula (N) were prepared starting from the corresponding racemic compound, the resolution being effected according to conventional methods by means of, for example, d(+)-camphosulphonic acid and d(−)-dibenzoyltartaric acid.

The compounds of formula I can be converted into addition salts with acids, which salts, as such, form part of the present invention.

There may be mentioned as acids for the formation of those salts, for example, in the mineral series hydrochloric, hydrobromic, sulphuric, nitric and phosphoric acid and, in the organic series, acetic, propionic, maleic, fumaric, tartaric, oxalic, benzoic, methanesulphonic and isethionic acid.

The compounds of formula I and their physiologically tolerable addition salts have valuable pharmacological and therapeutic properties, especially properties regulating the metabolism of glucides and lipids. Moreover, they cause a moderate reduction in arterial pressure.

More precisely, the compounds of the present invention improve the efficacy of insulin at a peripheral and-/or hepatic level, resulting in an improvement in glucose tolerance and in moderate hyperglycaemia, where it exists, without the risk of hypoglycaemia, as well as in a reduction in hyperinsulinaemia. Furthermore, the compounds of the invention reverse insulin-resistance induced by amylin.

They also reduce hypertriglyceridaemia and combat LDL (low density lipoprotein) oxidation, which has an implication in the prevention of macroangiopathies.

They cause a modest reduction in weight, associated with a reduction in food intake.

Those properties enable them to be used therapeutically especially for the treatment of non-insulin-dependent diabetics not treated by diet, non-insulin-dependent diabetics treated with blood sugar-reducing medicaments, diabetics who are insulin-dependent or not, treated with insulin, or non-hyperglycaemic, hypertensive or non-hypertensive patients having hyperinsulinaemia (i.e. android obesity) and all exhibiting a resistance to insulin which is or is not induced by amylin.

The products of the invention are thus used in the treatment of syndrome X (by way of improvement in the effect of insulin at the periphery and/or with respect to the liver, decrease in triglycerides and in LDL oxidation, associated with a moderate reduction in weight), and in the treatment of hypertension in patients who are resistant to insulin or have associated or non-associated metabolic anomalies, such as, for example, hyperinsulinaemia, dyslipaemia and hyperglycaemia, which are secondary or not to the effects of amylin.

The present invention also relates to pharmaceutical compositions containing as active ingredient a compound of the general formula I or a physiologically tolerable salt thereof, mixed with or in association with one or more appropriate pharmaceutical excipients.

The so-obtained pharmaceutical compositions are generally presented in dosage form containing from 25 to 50 mg of active ingredient. They may be in the form of tablets, dragées, capsules, suppositories or injectable or drinkable solutions, and may be administered by the oral, rectal or parenteral route.

The dosage may vary, especially in accordance with the age and weight of the patient, the route of administration, the nature of the disorder and associated treatments, and ranges from 25 to 50 mg of active ingredient per administration from 1 to 4 times per day.

The following Examples illustrate the invention.

EXAMPLE 1

Synthesis of (S)-1-(m-trifluoromethylphenyl)-2-{β-{4-[2-(N-(3,3-diphenylpropionyl)amino)ethyl]benzoyloxy}ethylamino}propane and its hydrochloride of a 10% NaHCO3 solution in the presence of 200 ml of ether. The organic solution is washed three times with 50 ml of water each time, dried over magnesium sulphate and concentrated in vacuo. 23.5 g of product are obtained which are chromatographed on silica using CH2Cl2/CH3COOH, 50/50, as eluant to yield 11.5 g of (S)-1-(m-trifluoromethylphenyl)-2-{β-{4-[2-(N-(3,3-diphenylpropionyl)amino)ethyl]benzoyloxy}-ethylamino}propane.

There are added to that base dissolved in 600 ml of anhydrous ether 4.4 ml of 4.16N ethereal hydrogen chloride in 200 ml of hexane. The resulting precipitate is suctioned-filtered, washed with petroleum ether and dried. 10.6 g of (S)-1-(m-trifluoromethylphenyl)-2-{β-{4-[2-(N-(3,3-diphenylpropionyl)amino)ethyl]benzoyloxy}ethylamino}propane hydrochloride, m.p. 90° C., are obtained.

The (S)-1-(m-trifluoromethylphenyl)-2-[N-benzyl-N-(β-chloroethyl)amino]propane starting material was prepared as follows:

a) 175.7 g (1 mol) of (S)-N-(1-m-trifluoromethylphenylprop-2-yl)-N-benzylglycine dissolved in 500 ml of tetrahydrofuran are added, over a period of 3 hours, with stirring, to 24 g of lithium aluminium hydride suspended in 500 ml of tetrahydrofuran. The temperature is maintained at 40°-42° C. After heating for 2 hours at 40°-45° C., the reaction mixture is hydrolysed with 25 ml of water, 25 ml of 4N NaOH, then with 75 ml of water. After suction-filtering and washing with tetrahydrofuran, the filtrate is concentrated to dryness using a vacuum pump. 166.5 g of (S)-1-(m-trifluoromethylphenyl)-2-[N-benzyl-N-(β-hydroxyethyl)amino]propane are obtained.

There are added to the resulting product, dissolved in 400 ml of anhydrous ethyl acetate and 150 ml of cyclo-

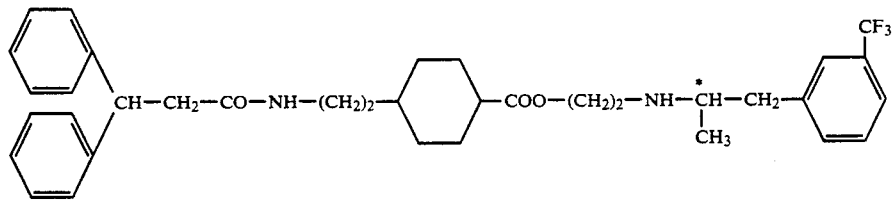

18.7 g of p-[2-(N-(3,3-diphenylpropionyl)amino)ethyl]benzoic acid dissolved in 280 ml of dimethylformamide are added with stirring, over a period of 1 hour, to 2.6 g of a 50% sodium hydride suspension in paraffin and 200 ml of anhydrous dimethylformamide, then the whole is heated for 30 minutes at 40° C.

17.8 g of (S)-1-(m-trifluoromethylphenyl)-2-(N-benzyl-N-(β-chloroethyl)amino)propane in 500 ml of dimethylformamide are then added and the reaction mixture is heated at 100° C. for 24 hours. After cooling, the solvent is evaporated off in vacuo. The residue is taken up 3 times in 100 ml of methylene chloride each time. Filtration and concentration yield 29.3 g of (S)-1-(m-trifluoromethylphenyl)-2-{N-benzyl-N-[β-{4-[2-(N-(3,3-diphenylpropionyl)amino)ethyl]benzoyloxy}ethyl]amino}propane.

The product so-obtained is taken up in 220 ml of acetic acid and the solution is hydrogenated in a PARR apparatus under 413×10³ Pa in the presence of 5 g of carbon black with 5% palladium, with heating at 50°-60° C., for 2 hours. After suction-filtering, the solvent is removed in vacuo, the residue is taken up in 200 ml of water and the solution is neutralised with 200 ml hexane, 113 ml of 4.6N ethereal hydrogen chloride. After suction-filtering, the product is washed with a mixture of ethyl acetate/cyclohexane (80/30), then with petroleum ether, and dried in air. 144.5 g of (S)-1-(m-trifluoromethylphenyl)-2-[N-benzyl-N-(β-hydroxyethyl)amino]propane hydrochloride, m.p. 129°-130° C., are obtained.

b) 37.4 g of this hydrochloride in 100 ml of anhydrous chloroform are added over a period of one hour, with stirring, to 8 ml of thionyl chloride and 25 ml of anhydrous chloroform. After slow heating to reflux, which is reached at the end of 1 hour 30 minutes, refluxing is maintained for 1 hour. After cooling and concentration in vacuo, the residue is recrystallised from 220 ml of boiling ethyl acetate and diluted with 280 ml of cyclohexane. 20 g of (S)-1-(m-trifluoromethylphenyl)-2-[N-benzyl-N-(β-chloroethyl)amino]propane hydrochloride, m.p. 130°-132° C., are obtained. 19.7 g of that hydrochloride, dissolved in 400 ml of water, are rendered alkaline with 7.5 ml of a 36° Baumé sodium hydroxide solution in the presence of 400 ml of ether. The organic layer is decanted off and concentrated in vacuo.

17.9 g of (S)-1-(m-trifluoromethylphenyl)-2-[N-benzyl-N-($\beta$-chloroethyl)amino]propane in the form of a base are obtained.

EXAMPLE 2
Pharmacological Study

A. Study of the Effect of a Chronic Treatment Administered Per OS to 52-Week-Old Male SDCD Rats

1. Aim of the experiment

The tests are carried out on rats that have weight anomalies associated with hyperinsulism and hyperglyceridaemia.

The following are investigated:

on the one hand the effect of a prolonged treatment with the product of Example 1 and the reference substances on those anomalies, and on the other hand the consumption of glucose by the adipose tissue is measured in the basal state and in the presence of insulin ($10-9M$).

2. Protocol

2.1 Animals used

In this experiment, adult male SPRAGUE DAWLEY rats were used in groups of 5 to 12 animals.

The rats used, aged 52 weeks, exhibit
- a reduction in glucose tolerance,
- an increase in basal insulinaemia, and
- an increase in plasma lipids.

The housing (from 9 to 52 weeks) of these rats was effected in a chamber at a temperature regulated at from 21° to 22° C. which was subjected to a fixed cycle of light (from 7.30 to 19.30 hours) and darkness (from 19.30 to 7.30 hours). Their food consisted of a maintenance diet (UAR A 03); water and food were supplied "ad libitum", with the exception of the night-fasting preceding the tests, when the food was removed.

2.2 Methods 9 days before the beginning of the experiment (d-9), the rats are divided into groups by randomisation based on weight.

5 days before the beginning of the experiment (d-5) the rats are conditioned by administering a gum solution.

The first day of the experiment (d1), the products to be tested are administered to the rats at different doses twice per day. More precisely, the products are administered suspended in the gum between 9.00 and 10.00 hours and 16.00 and 17.00 hours for 14 days. The treated animals are weighed daily.

On day 15 the rats (fasted for 18 hours) are sacrificed by decapitation. The blood is immediately collected in a cupule. An amount (50 $\mu$l) is transferred into 500 $\mu$l of uranyl acetate for determining the glycaemia. An amount of 3 ml is transferred into a tube containing a solution of heparin (30 $\mu$l per 1 ml of whole blood) and centrifuged to separate the plasma. Another amount of 300 $\mu$l is transferred to a tube containing 15 $\mu$l of a solution of EDTA/NaF for determining the lactates.

Epididymal adipose tissue is taken for metabolic study immediately after sacrifice.

For each animal, two fragments of right and left epididymal tissue are minced with scissors and distributed in 6 incubation flasks. Three of those flasks contain 500 $\mu$l of medium and the others 500 $\mu$l of medium to which porcine insulin ($10^{-9}$M) has been added; the production of $CO_2$ is thus measured in triplicate for each of the rats from each group.

2.3 Results

The results are given in the following Table I.

TABLE I

| Treatment of 52-week-old male SDCD rats | % weight change | Basal insulinaemia $\mu$U/ml % change | Glycaemia g/l % change | Glucose tolerance K $10^{-2}$ % change | Triglyceride g/l % change | Cholesterol g/l % change |
|---|---|---|---|---|---|---|
| Control | +0.4% | 32 ± 2.4 | 1.06 ± 0.05 | 3.01 ± 0.24 | 3.64 ± 0.57 | 1.1 ± 0.14 |
| Benfluorex | | | | | | |
| 1 mg/kgx2 | −2% (NS) | −10% NS | −10% NS | +30% $p < 0.05$ | −43% $p = 0.025$ | −20% NS |
| 2.5 mg/kgx2 | −6% $p = 0.85$ | −16% NS | −12% NS | +25% $p = 0.05$ | −44% $p = 0.05$ | −30% NS |
| Product of Example 1 | | | | | | |
| 1.0 mg/kgx2 | −1.4% $p = 0.01$ | −15% NS | +8% NS | +23% p $p < 0.05$ | −10% NS | 0% |
| 2.5 mg/kgx2 | −3% $p = 0.05$ | −26% $p = 0.09$ | 0% | +30% $p < 0.05$ | −20% $p = 0.09$ | 0% |

B. In Vitro Study of LDL Oxidation

A comparative study between the product of Example 1 and the reference substances (benfluorex, dimethyl biguanide) with respect to in vitro LDL oxidation was carried out.

The results are given in the following Table II.

TABLE II

| Control | In vitro LDL oxidation | | Incorporation of oleate in the esters of cholesterol |
|---|---|---|---|
| | by copper | by monocytes | |
| Benfluorex | inactive at $10^{-4}$M | inactive at $10^{-4}$M | −30% at $10^{-5}$M |
| Dimethyl biguanide $10^{-4}$M | inactive at $10^{-4}$M | inactive at $10^{-4}$M | inactive at $10^{-5}$M |
| Product of Example 1 | $IC_{50}$ = 5 × $10^{-5}$M | $IC_{50}$ = 5 × $10^{-5}$M | −70% at $10^{-5}$M |

C. Examination of the Hypotensive Effect in Conscious Dogs

The arterial pressure was measured by external pressure band (sphygmomanometer) on the tail of the dog, before and after treatment with the product of Example 1 at a dose of 5 mg/kg p.o..

The results are given in the following Table III.

TABLE III

| Product tested | Animal treated (number:n) | Decrease in arterial pressure (AP) | |
|---|---|---|---|
| | | systolic AP | diastolic AP |
| Product of Example 1 (5 mg/kg p.o.) | dog (n = 4) | −15 to −22 (mmHg) | −20 to −27 (mmHg) |

D. Conclusion

The results of the studies described above show the pharmacological and therapeutic value of the dextrorotatory isomer (or S-enantiomer) of 1-(m-trifluoromethylphenyl)-2-{β-{4-[2-(N-(3,3-diphenylpropionyl)amino)ethyl]benzoyloxy}ethylamino}propane hydrochloride (product of Example 1) and the novelty and superiority thereof compared with reference substances known to be specifically adapted to the treatments in questions.

We claim:

1. A compound selected from ethanolamine benzoate compounds of formula I:

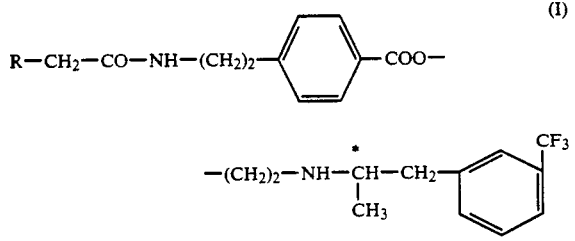

in which R represents:

a) a radical of the formula:

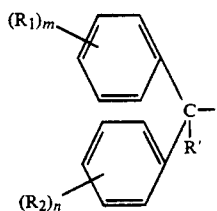

wherein:

R' represents hydrogen or straight-chain or branched alkyl containing 1 to 5 carbon atoms inclusive, $R_1$ and $R_2$, which are the same or different, each represents hydrogen or straight-chain or branched alkyl or alkoxy having 1 to 5 carbon atoms inclusive, and m and n, which are the same or different, each represents 1, 2 or 3;

b) or a fluorenyl radical of the formula:

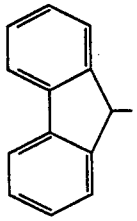

in the form of a racemic compound or an enantiomer, and addition salt thereof with a pharmaceutically-acceptable acid.

2. A compound of claim 1 which is: S-1-(m-trifluoromethylphenyl)-2-{β-{4-[2-(N-(3,3-diphenyl propionyl)amino)ethyl]benzoyloxy}ethylamino} propane hydrochloride.

3. A pharmaceutical composition, useful for treating syndrome X, a hyperamylinemia, a decrease in glucose tolerance, hyperinsulinaemia, dyslipaemia, or hypertension, and for treating hypertension in patients who are insulin-resistant or have one or more metabolic anomalies, containing, as active ingredient, an effective amount of at least one compound of claim 1, in combination with one or more pharmaceutically-acceptable excipients.

4. A method for treating a mammal afflicted with syndrome X, a hyperamylinemia, a decrease in glucose tolerance, hyperinsulinaemia, dyslipaemia, or hypertension, or afflicted with hypertension in patients who are insulin-resistant or have one or more metabolic anomalies, comprising the step of administering to the said mammal an amount of a compound of claim 1 which is effective for the alleviation of the said condition.

5. A compound of claim 1 which is selected from: S-1-(m-trifluoromethylphenyl)-2-{β-{4-[2-(N-(3,3-diphenylpropionyl)amino)ethyl]benzoyloxy}ethylamino} propane and a pharmaceutically-acceptable acid addition salt thereof.

* * * * *

UNITED STATES PATENT AND TRADEMARK OFFICE
CERTIFICATE OF CORRECTION

PATENT NO. : 5,266,591

DATED : Nov. 30, 1993

INVENTOR(S) : Michel Wierzbicki, Pierre Hugon, Jacques Duhault, Michelle Boulanger, Francoise Lacour It is certified that error appears in the above-identified patent and that said Letters Patent is hereby corrected as shown below:

Column 2, approximately line 8, 9; "wherein: represents, inter alia," should read -- wherein: - n represents, inter alia, --.

Column 11, line 21; "(10-9M)." should read -- $(10^{-9} M)$. --.

Column 14, line 48; move the "e" from the end of line 49 to the beginning of line 50 and insert before "thylamino".

Signed and Sealed this

Fourteenth Day of June, 1994

Attest:

BRUCE LEHMAN

Attesting Officer   Commissioner of Patents and Trademarks